(12) United States Patent
Sievers et al.

(10) Patent No.: US 6,414,196 B1
(45) Date of Patent: Jul. 2, 2002

(54) PROCESS AND DEVICE FOR PREPARING PURE FORMALDEHYDE

(75) Inventors: Werner Sievers, Frankfurt; Elke Schweers, Bad Soden; Michael Rosenberg, Niedernhausen, all of (DE)

(73) Assignee: Ticona GmbH, Kelsterbach (DE)

( * ) Notice: Subject to any disclaimer, the term of this patent is extended or adjusted under 35 U.S.C. 154(b) by 0 days.

(21) Appl. No.: 09/530,441

(22) PCT Filed: Oct. 12, 1998

(86) PCT No.: PCT/EP98/06443

§ 371 (c)(1),
(2), (4) Date: May 25, 2000

(87) PCT Pub. No.: WO99/21818

PCT Pub. Date: May 6, 1999

(30) Foreign Application Priority Data

Oct. 29, 1997 (DE) .......................................... 197 47 647

(51) Int. Cl.⁷ .............................................. C07C 45/00

(52) U.S. Cl. ........................................ 568/493; 568/449

(58) Field of Search .................................. 568/449, 453

(56) References Cited

U.S. PATENT DOCUMENTS 2,943,701 A * 7/1960 Funck et al. ................ 183/115

* cited by examiner

*Primary Examiner*—Sreeni Padmanabhan
(74) *Attorney, Agent, or Firm*—Connolly Bove Lodge & Hutz LLP

(57) ABSTRACT

A process for the post-purification in particular of pyrolysis gases for preparing pure formaldehyde, hemiformal being pyrolyzed in an evaporator, the resulting formaldehyde vapor being passed through a condensed liquid component collected in the bottom area of the evaporator, the condensed liquid component being passed out as a falling film situated on the inner wall through a cooled outlet tube disposed in the bottom area of the evaporator and the formaldehyde vapor being passed through the cooled outlet tube in cocurrent and the liquid component and the formaldehyde being taken off separately at the outlet tube end remote from the evaporator.

9 Claims, 1 Drawing Sheet

PROCESS AND DEVICE FOR PREPARING PURE FORMALDEHYDE

This application is a 371 of PCT/EP98/06443 filed Oct. 12, 1998 now WO99/21818 published May 6, 1999.

The present invention relates to a process and an apparatus for the post-purification in particular of pyrolysis gases for preparing pure formaldehyde.

To prepare engineering plastics (polyacetals, polyoxymethylene), high-purity formaldehyde is required. The quality of the plastic produced, which should be of as high a molecular weight as possible, primarily depends on the purity of the gaseous formaldehyde, in addition to the polymerization conditions selected. Various processes for preparing formaldehyde from methanol are known (e.g. Oxidation in the formox process, oxidative dehydrogenation, direct dehydrogenation of methanol) which deliver formaldehyde in liquid (aqueous) or gaseous phase. Regardless of the phase state (gaseous or liquid), formaldehyde never arises as a pure substance, but in a mixture with water and other byproducts. However, both the anionic and cationic polymerization require gaseous formaldehyde which must contain only minimal amounts of the minor components which are harmful to or disrupt the respective polymerization.

What are termed the hemiformal processes are known for preparing high-purity gaseous formaldehyde. In these processes, aqueous formaldehyde (approximately 40–70% by weight water) reacts with an alcohol, forming hemiformals: e.g. with cyclohexanol, forming cyclohexyl hemiformals and possibly polyformals. The reaction appears as follows:

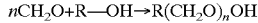

$$n CH_2O + R-OH \rightarrow R(CH_2O)_nOH$$

The alcohols used should not contain reactive groups such as carbonyl, nitro or amino groups, which can participate in unwanted side reactions. Monohydric or polyhydric alcohols can be used whose boiling point is advantageously markedly above that of water. Cyclohexanol is advantageous.

The hemiformal mixture can be separated from water by distillation, the overhead vapors, after condensation, forming a two-phase mixture of water and cyclohexanol. The bottom product is the desired hemiformal, containing small amounts of water, methanol, methyl formate and other byproducts.

After removal of byproducts, the hemiformal is thermally cleaved at 1 to 1.5 bar and 120 to 180° C. (pyrolysis, thermolysis). The resulting formaldehyde vapors, if they are not yet sufficiently low in byproducts, are post-purified in a further process stage. Here, both scrubbing processes (gas flows in the opposite direction to a falling film) and prepolymerization processes are known for separating off methanol and water. In the scrubbing processes, the absorption capacity of certain alcohols is exploited (accepting significant losses of formaldehyde), and in the prepolymerization processes the fact that, in the polymerization of formaldehyde on cold surfaces, as in RU 262 45 42 or DD 124 92 48, or cold liquids, as described in DE 115 94 20, an increased separation of minor components can be observed is exploited (accepting the accompanying solids problem). In the prepolymerization, owing to the spontaneous formation of low-molecular-weight polymer, water and other components are removed from the reaction medium by the resulting end groups.

Customarily, the pyrolysis is carried out in an evaporator, e.g. a falling-film evaporator. The formaldehyde vapors are taken off at the top of the evaporator. Thereafter, the vapors are forced in cocurrent or countercurrent through tubes, down the inner wall of which a trickling film of laden cyclohexyl hemiformal runs. The trickling film is usually cold (0 to 50° C.) and absorbs the interfering byproducts (e.g. methanol, water and methyl formate), but also formaldehyde, which leads to quantitative losses at the level of up to 30% of the formaldehyde used. Processes of this type are described, for example, in U.S. Pat. No. 2,848,500 or U.S. Pat. No. 2,943,701. Usually, only smooth tubes are used, because other geometries (e.g. packed columns or plate columns) cannot be cleaned in the event of unwanted polymerization. In addition, other absorption processes are known, e.g. using poly(ethylene glycol ester)s from GB 221 8089.

Since polymerization can also be observed in the pyrolysis, considerable efforts have been made to overcome the solids problem. Thus, pyrolysis apparatuses have been developed in the form of plate columns which comprise individually heated plates, occasionally having special heatable geometries, and are described, for example, in DD 254 847, DE 521 33 or DD 124 98 46. For post-purification, processes have been developed in which a heated rotor is used in the falling-film evaporator, disclosed in DD 333 11 91. In order to exploit the prepolymerization effect specifically, low-temperature apparatuses (−20° C.) have been developed in which two heatable screws engage with one another and discharge resulting solids, disclosed by DD 124 92 48.

In order to separate off the byproducts, which are present in the cyclohexyl hemiformal solution, from the liquid, in addition to the above-described distillation processes, adsorption processes have also been developed, e.g. using ion exchangers for adsorbing formic acid and methyl formate, disclosed in DD 118 64 53, IT 119 61 75 or IT 311 87 47.

In order to decrease the byproduct formation in the pyrolysis, which is frequently carried out at high temperatures of 150 to 180° C., processes are known in which salts are added to the cyclohexyl hemiformal solution. Adding salt can suppress the formation of high-boiling substances, disclosed by U.S. Pat. No. 6,705,098 or U.S. Pat. No. 6,705,100; on the other hand, problems with salt encrustation on heat exchangers etc. occur.

For the post-purification of the gaseous formaldehyde, a process is also disclosed, for example, by JP 413 70 54, DE 305 17 55 or IT 318 49 00, in which water is separated off from the gas mixture by adsorption using dry beads or other adsorbents (silica gel, zeolites). In this process as well, the formaldehyde loss is very high, since formaldehyde is adsorbed on adsorbents of this type.

Temperature and pressure are fundamentally critical for an optimum pyrolysis. The boiling temperature of the alcohol provided for the hemiformal formation should therefore be at a sufficient distance from the pyrolysis temperature.

However, all these known processes for the post-purification of gaseous formaldehyde have the disadvantage of an increased equipment requirement, owing to a sometimes highly complicated structure using different coupled apparatuses, and high formaldehyde losses, and in some cases also exhibit unsatisfactorily high residual contamination.

Against this background, the object of the present invention is therefore to provide a process for the post-purification in particular of pyrolysis gases for preparing pure formaldehyde, which process overcomes the described disadvantages, and an apparatus for carrying out the process.

This object is achieved according to the invention by a process for the post-purification in particular of pyrolysis gases for preparing pure formaldehyde, having the process steps of:

pyrolyzing of hemiformal in an evaporator, passing the resulting formaldehyde vapor through the condensed liquid component collected in the bottom area of the evaporator, passing out the condensed liquid component through a cooled outlet tube disposed in the bottom area of the evaporator, so that the condensed liquid component flows down as a falling film on the inner wall of the cooled outlet tube, passing the formaldehyde vapor in cocurrent through the cooled outlet tube, taking off the formaldehyde vapor at the outlet tube end remote from the evaporator, and taking off the condensed liquid component at the outlet tube end remote from the evaporator.

Although this process can be carried out with any desired evaporator, pyrolysis is advantageously carried out in a thin-film evaporator. The resulting vapors are according to the invention no longer taken off at the top end of the evaporator, that is overhead, but are ejected in what is termed the bottom liquid-phase area of the evaporator together with the condensed liquid component. From this liquid phase disposed in the bottom area of the evaporator there exits a cooled outlet tube in which, firstly, the condensed liquid component flows down as a falling film on the inner wall of the outlet tube; in the case of the pyrolysis of hemiformal, this component consists principally of alcohol, e.g. cyclohexanol. Secondly, the resulting formaldehyde vapor is passed, preferably in cocurrent, through the cooled outlet tube and taken off at the outlet tube end remote from the evaporator.

The formaldehyde vapor ejected at the bottom end of the evaporator in its liquid-phase area and passed through the cooled outlet tube in cocurrent to the failing alcohol film stabilizes both the falling film in the evaporator and that in the outlet tube, the tendency to foaming being markedly decreased here in the evaporator in particular. A cocurrent mode of operation furthermore markedly decreases the entrainment of alcohol droplets, which largely obviates the need to use demisters or condensers, in contrast to the countercurrent mode of operation.

The byproduct separation or post-purification already takes place here in the liquid phase or in the bottom-product discharge of the thin-film evaporator. Here, at high temperature, gas and liquid are then in direct contact, the temperature in this case still being close to the pyrolysis temperature which is generally between 100 and 200° C., advantageously between 145 and 165° C., so that no hemiformals are formed but, on the other hand, minor components are already physically absorbed. The transition zone between the hot evaporator and the cold outlet tube is extremely short, the temperature of the cooled outlet tube generally being between −20° C. and +40° C., advantageously between 0 and 20° C. The cold outlet tube serves for fine purification, the outlet tube generally being essentially short in order to keep the formaldehyde losses small. Finally, the formaldehyde losses due to absorption are also less, since the process pressure is in the vacuum range, advantageously between 600 and 900 mbar, so that the partial pressure of formaldehyde is less than 1 bar.

In a development, it is also possible to transport the condensed liquid component into the outlet tube using a transport apparatus.

In another development, it is also possible to take off a partial stream of the condensed liquid component which is low in minor components (e.g. trioxane) from the bottom area of the evaporator, while the other partial stream of the condensed liquid component is passed through the cooled outlet tube disposed in the bottom area of the evaporator, has a higher content of minor components (e.g. trioxane) after flowing through the outlet tube, and is taken off at the outlet tube end remote from the evaporator. In this manner, it is possible to use the two liquid partial streams further at different points of the process according to their differing content of minor components.

It is further possible to fit, between the pyrolysis zone and the takeoff of the condensed liquid component which is low in minor components, a cooling zone which is operated at temperatures high enough that only some of the vaporized alcohol, e.g. cyclohexanol, resulting after elimination of formaldehyde from the hemiformal is condensed. In this manner, higher temperatures may advantageously be set in the pyrolysis, in order to achieve higher rates of elimination of formaldehyde from the hemiformal and simultaneously to have available for the takeoff a sufficiently large stream of condensed liquid component which is low in minor components.

The apparatus for carrying out the process for the post-purification in particular of pyrolysis gases for preparing pure formaldehyde according to the invention has an outlet tube which can be disposed in a bottom area of an evaporator, the outlet tube preferably being coolable and having a takeoff for taking off the vapors formed in the evaporator.

A particularly simple and thus inexpensive apparatus for carrying out the described process is thus provided, since here, in comparison with the previously known processes, alcohol vapor can be recondensed in one apparatus. In the previously known processes which are extensively described above, for this purpose, individual apparatuses are necessary in each case, namely evaporator, falling film tube and a downstream condenser for recondensation of entrained alcohol. In addition, pumps are necessary here which transport the alcohol for producing a falling film into the post-purification apparatus or the falling film tube.

Even though the coolable outlet tube can be disposed in the bottom area of any desired evaporator, it is, however, preferably disposed in the bottom area of a thin-film evaporator. If then the evaporator is further advantageously constructed in the bottom area for collecting the condensed liquid component, the formaldehyde vapor produced can be passed, as described and according to the process, through this area termed liquid phase, for post-purification.

The condensed liquid component collected in this liquid phase can be transported to the cooled outlet tube when, according to a preferred embodiment, an apparatus for the outflow of the condensed liquid component is disposed in the liquid phase. In this manner, the falling film can be produced particularly easily on the inner wall of the cooled outlet tube and continuously maintained, as a result of which the post-purification considerably improved. If appropriate, the condensed liquid components can also be transported using a transport apparatus. This transport apparatus can be constructed, for example, as a screw conveyor.

By means of this apparatus, the cocurrent flow of the formaldehyde vapor with the falling film in the cooled outlet tube, provided according to the process, can be particularly easily implemented if advantageously a takeoff for taking off the vapors is disposed at the outlet tube end remote from the evaporator. Finally, cooling the outlet tube is possible easily and without problem if, according to a further preferred embodiment, the outlet tube is constructed to have a double wall.

The formaldehyde prepared by the process according to the invention is suitable for all known fields of application, for example corrosion protection, mirror manufacture, electrochemical coatings, for disinfection and as a preservative, likewise as an intermediate for preparing plastics, for example polyoxymethylenes, polyacetals, phenolic resins, melamines, amino resins, polyurethanes and casein plastics, 1,4-butanols, alcoholic formaldehyde solutions, methylal, trimethylolpropane, neopentyl glycol, pentaerythritol and trioxane, for preparing dyestuffs, such as fuchsin, acridine, for preparing fertilizers, and for treating seeds.

The invention also relates to trioxane, dyestuffs, fertilizers and plastics, such as polyoxymethylene and polyacetals, prepared in this manner, and seeds treated in this manner.

The process is described in more detail below with reference to examples.

The hemiformal solutions pyrolyzed in the examples were cyclohexyl hemiformals. For this purpose, gaseous formaldehyde, which had been prepared as a crude gas in a mixture with inerts from a methanol dehydrogenation or from a laboratory cleavage of trioxane, was brought into contact with cyclohexanol for hemiformal formation in a plate column. The solutions comprised approximately 200–300 g of formaldehyde (as hemiformal) per liter of solution. For the pyrolysis, a DN50 Rotafilm thin film evaporator having a heating area of 0.05 m² was used. When the product was taken off at the bottom according to the invention, a tube of length 250 mm and internal diameter 25 mm was situated directly beneath the product discharge of the thin-film evaporator, which tube could be cooled externally via a jacket. This tube contained the failing film for post-purification. When the product was taken off at the top end of the thin-film evaporator, as previously known, the formaldehyde vapors were passed through tubing into a falling film tube in order to be post-purified.

In the examples below, the gas composition was measured by a gas chromatograph. Since the gas chromatograph cannot measure byproducts in a pure formaldehyde atmosphere, the stream fed to the gas chromatograph was diluted with nitrogen. Accordingly, the tables below report the measured and dilution-corrected concentration values.

Firstly, the process according to the invention was carried out with vapor taken off at the bottom, the evaporator being operated at various pressures and temperatures. The temperature of the cooled outlet tube was also varied. The results are summarized in Table 1.

TABLE 1

Experiment: FAR01
Product taken off at the bottom
Thin-film evaporator Rotafilm DN50 having 0.05 m2
Falling film: tube length 250 mm

| Feed: | Vol. flow rate | 0.2 l/h |
| | Formald. | 240 g/l |
| Speed: | 900 rpm | |

| Pressure evaporator [mbar] | Temperature evaporator [° C.] | Temperature falling film [° C.] | Formaldehyde vapor flow rate [l/h] | Formaldehyde [%] | Water [ppm] | Methanol [ppm] | Methyl formate [ppm] |
|---|---|---|---|---|---|---|---|
| 800 | 150 | 20 | 20 | 40 | 2000 | 20 | 1000 |
| 600 | 145 | 0 | 20 | 40 | 1800 | 15 | 1000 |
| 600 | 170 | −9 | 17 | 50 | 1500 | 12 | 2200 |
| Corrected to 100% formaldehyde, since originally diluted with nitrogen: | | | | | | | |
| 800 | 150 | 20 | 20 | 100 | 5000 | 50 | 2500 |
| 600 | 145 | 0 | 20 | 100 | 4500 | 38 | 2500 |
| 600 | 170 | −9 | 17 | 100 | 3000 | 24 | 4400 |

In the product gas, methanol concentrations of only 24 ppm could be achieved. It can readily be seen that post-purification improves with decreasing temperature in the falling film. Although byproduct formation increases in the thin-film evaporator owing to the temperature jump from 145 to 170° C., in the case of methanol this can readily be compensated for by the process described. Furthermore, it can be shown that the formaldehyde loss between 20 and 0° C. in the falling film is minor (20 l/h of product in each case). The falling film should therefore be advantageously operated at 0 to 10° C.

In Example 2, the vapor, according to the prior art, was taken off at the top of the thin-film evaporator and not post-purified. The results of this example are listed in Table 2.

TABLE 2

Experiment: PYR9
Product taken off at the top
Thin-film evaporator Rotafilm DN50 having 0.05 m2

| Feed: | Vol.flow rate: | 0.4 l/h |
| | Formald.: | 160 g/l |
| Speed: | 900 rpm | |

| Pressure evaporator | Temperature evaporator | Formaldehyde vapor | Formalde- | Methanol | Methyl |

TABLE 2-continued

| [mbar] | [° C.] | flow rate [l/h] | hyde [%] | [ppm] | formate [ppm] |
|---|---|---|---|---|---|
| 800 | 154 | 7.5 | 70 | 350 | 1000 |
| 600 | 144 | 7.5 | 70 | 300 | 1000 |
| 400 | 125 | 4 | 20 | 250 | 300 |
| 100 | 125 | 1 | 8 | 300 | 90 |
| Corrected to 100% formaldehyde, since originally diluted with nitrogen: | | | | | |
| 800 | 154 | 7.5 | 100 | 500 | 1429 |
| 600 | 144 | 7.5 | 100 | 429 | 1429 |
| 400 | 125 | 4 | 100 | 1250 | 1500 |
| 100 | 125 | 1 | 100 | 3750 | 1125 |

The methanol concentrations are in the range of several 100 ppm. From this example, an optimal mode of operation for the pyrolysis can be indicated. At a pressure of 600 to 800 mbar and a temperature of 145 to 160° C., cyclohexyl hemiformal can be pyrolyzed with maximum yield (see formaldehyde flow rates in Table 2) and low byproduct contents.

In Example 3, the gas was taken off at the top of the thin-film evaporator and passed via tubing to a 250 mm long tube piece, which was firstly cooled to 20° C. and then to 0° C. A weak trickling film of condensed cyclohexanol forms, which itself has a post-purification effect, see Table 3.

TABLE 3

Experiment: PYR13
Product taken off at the top
Thin-film evaporator Rotafilm DN50 having 0.05 m2
Falling film: Tube length 250 mm

| Feed: | Vol.flow rate: | 0.2 l/h |
| | Formald.: | 270 g/l |
| Speed: | 900 rpm | |

| Pressure evaporator [mbar] | Temperature evaporator [° C.] | Temperature falling film [° C.] | Formaldehyde vapor flow rate [l/h] | Formaldehyde [%] | Water [ppm] | Methanol [ppm] | Methyl formate [ppm] |
|---|---|---|---|---|---|---|---|
| 800 | 145 | 20 | 11 | 35 | 1500 | 45 | 400 |
| 800 | 145 | 0 | 11 | 35 | 1500 | 45 | 400 |
| Corrected to 100% formaldehyde, since originally diluted with nitrogen: | | | | | | | |
| 800 | 145 | 20 | 11 | 100 | 4286 | 129 | 1143 |
| 800 | 145 | 0 | 11 | 100 | 4286 | 129 | 1143 |

In Example 4, although the product was taken off at the bottom according to the invention, it was not then passed into a falling-film tube flanged directly to the thin-film evaporator, but was conducted via tubing to a separate tube. The tube, measuring 1 m in length and 25 mm in diameter, can be cooled externally. The post-purification in this tube used as a falling-film apparatus was performed according to U.S. Pat. No. 2,943,701. For this purpose, a laden cyclohexyl hemiformal mixture was pumped at 0° C. to the top of the tube in order to run down as a trickling film on the inner wall of the tube. The pyrolysis gas was forced through the tube in countercurrent thereto from bottom to top. The gas concentrations were each determined directly after the pyrolysis and after the post-purification, see Table 4.

TABLE 4

Experiment: PYR12
Product taken off at the bottom
Thin-film evaporator Rotafilm DN 50 having 0.05 m2
Externally produced falling film: tube length 1000 mm, DN25, in accordance with Patent H25

| Feed: | Vol.flow rate: | 0.2 l/h |
| | Formald.: | 282 g/l |
| Speed: | 900 rpm | |
| Pressure evaporator | 800 mbar | |
| Temperature evaporator | 155° C. | |
| Temperature falling film | 0° C. | |

| | Formaldehyde vapor flow rate [l/h] | Formaldehyde [%] | Methanol [ppm] | Methyl formate [ppm] |
|---|---|---|---|---|
| Before falling film | 45 | 100 | 150 | 4500 |
| After falling film | 8 | 100 | 360 | 2000 |

The formaldehyde losses were enormously high. Approximately 80% of the formaldehyde produced was reacted to form hemiformals. Since the gas stream decreased on account of this from 45 l/h to 8 l/h, the methanol content actually increased from 150 to 360 ppm.

BRIEF DESCRIPTION OF THE DRAWINGS

An apparatus for carrying out the process is described with reference to FIG. 1, which shows a diagrammatic depiction: the figure shows a thin-film evaporator 1 which has a hemiformal feed line 3 at the top end. The lower area of the thin-film evaporator 1 is constructed as liquid-phase area 15. The liquid-phase area 15 opens into an outlet tube 5, which is here of double-wall construction and has a coolant feed line 7 and a coolant outlet line 9, through which, for cooling, the coolant is conducted in and out. At the bottom end of the outlet tube 5, a takeoff 11 is further disposed for passing out the high-purity formaldehyde gas. Finally, the outlet tube 5 has, at the bottom end, a further takeoff 13 for the condensed liquid component. In addition, a takeoff 17 is fitted for a partial stream of the condensed liquid component from the liquid-phase area 15 of the thin-film evaporator 1.

The hemiformal is passed via the feed line 3 to the thin-film evaporator 1 and pyrolyzed. In the course of this, the condensed liquid components, here in particular alcohol, e.g. cyclohexanol, collect in the liquid-phase area 15. This alcohol is passed from the liquid-phase area 15 to the outlet tube 5, with it flowing down the inner wall thereof as a falling film. A partial stream of the condensed liquid components can be taken off via the takeoff 17 and fed to another process step. The formaldehyde vapors formed in the evaporator are likewise passed through the liquid-phase area 15 into the outlet tube 5 and conducted there in cocurrent to the falling alcohol film to the takeoff 11. There, they are taken off and passed on to the polymerization as high-purity formaldehyde gas. The alcohol passed out in the outlet tube 5 as a falling film is withdrawn through the takeoff 13 and fed to another process step. The outlet tube 5 is cooled in this case via a cooling circuit to which the outlet tube 5 is connected by the coolant feed line 7 and the coolant outlet line 9.

Figure 1:
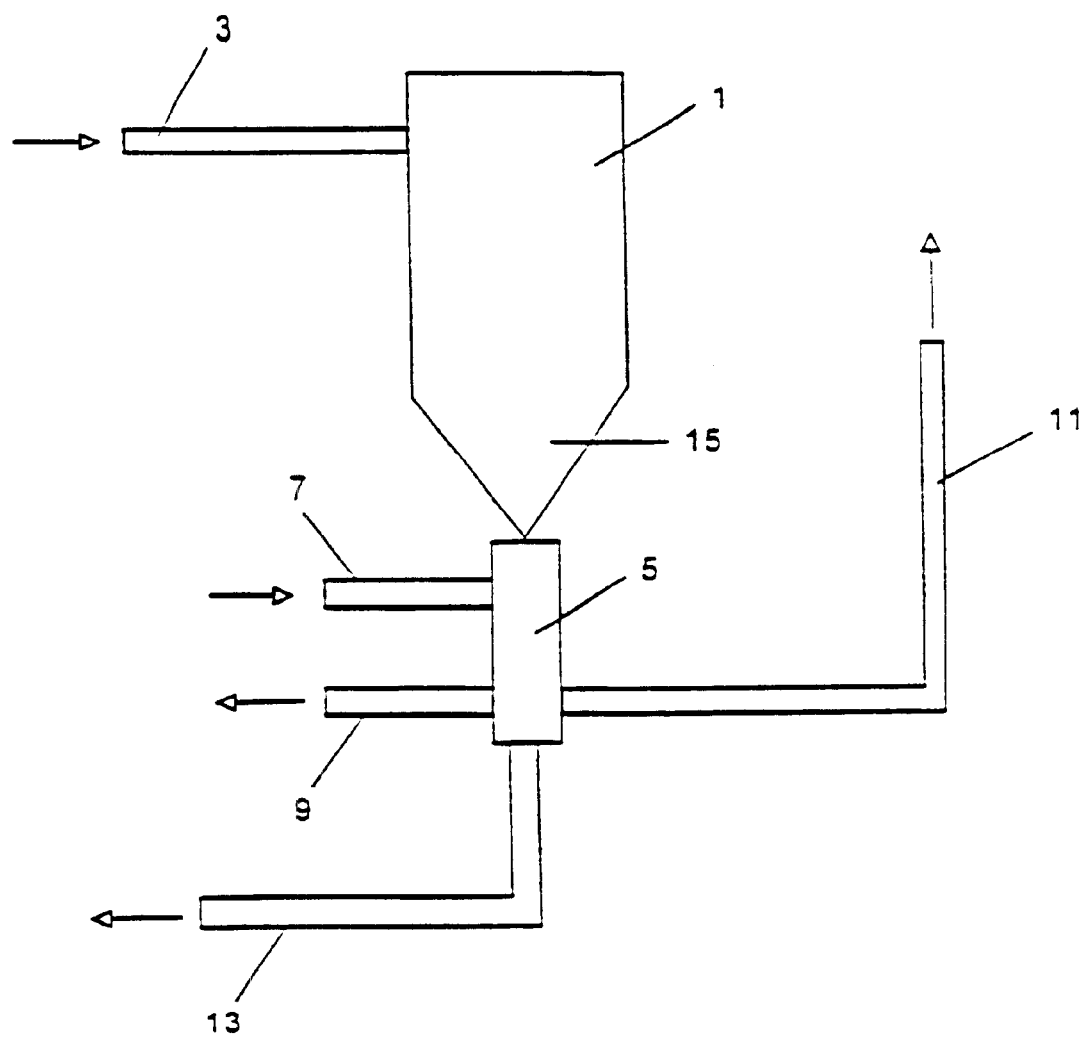

By means of this described apparatus, it is possible to carry out in one apparatus pyrolysis and post-purification of the formaldehyde vapor produced. This markedly reduces the equipment requirement, so that overall the costs are markedly reduced. Furthermore, when this apparatus is used and the process described is used, only low formaldehyde losses arise, and a high gas purity is achieved. Thus, it is possible to prepare, for example, gaseous formaldehyde having methanol contents below 40 ppm.

LIST OF REFERENCE NUMERALS

1 Thin-film evaporator
3 Hemiformal feed line
5 Outlet tube
7 Coolant feed line
9 Coolant outlet line
11 High-purity formaldehyde gas takeoff
13 Condensed liquid component takeoff downstream of the outlet tube
15 Liquid phase
17 Condensed liquid component takeoff from the evaporator liquid phase

What is claimed is:

1. A process for the post-purification of pyrolysis gases for preparing pure formaldehyde, having the process steps of:
   pyrolyzing hemiformal in an evaporator,
   passing the resulting formaldehyde vapor through the condensed liquid component collected in the bottom area of the evaporator,
   passing out the condensed liquid component through a cooled outlet tube disposed in the bottom area of the evaporator, so that the condensed liquid component flows down as a falling film on the inner wall of the cooled outlet tube,
   passing the formaldehyde vapor in cocurrent through the cooled outlet tube,
   taking off the formaldehyde vapor at the outlet tube end remote from the evaporator, and
   taking off the condensed liquid component at the outlet tube end remote from the evaporator.

2. A process for the post-purification of pyrolysis gases comprising minor components for preparing pure formaldehyde, having the process steps of:
   pyrolyzing of hemiformal in an evaporator,
   passing the resulting formaldehyde vapor through the condensed liquid component collected in the bottom area of the evaporator, which is low in minor components,
   precooling the vapor, so that some of the vaporized alcohol present after elimination of formaldehyde from the hemiformal is condensed,
   taking off some of the condensed liquid component which is low in minor components from the bottom area of the evaporator,
   taking off some of the condensed liquid component which is low in minor components from the bottom area of the evaporator,
   passing out the other portion of the condensed liquid component through a cooled outlet tube disposed in the bottom area of the evaporator, so that this portion of the condensed liquid component flows down as a falling film on the inner wall of the cooled outlet tube,
   passing the formaldehyde vapor in cocurrent through the cooled outlet tube,
   taking off the formaldehyde vapor at the outlet tube end remote from the evaporator, and
   taking off the other portion of the condensed liquid component, which after flowing through the outlet tube has a higher content of minor components, at the outlet tube end remote from the evaporator.

3. The process as claimed in claim 1, wherein the condensed liquid component runs out spontaneously (by gravity) into the outlet tube.

4. The process as claimed in claim 1, wherein the condensed liquid component is transported into the outlet tube using a transport apparatus.

5. The process as claimed in claim 1, wherein the pyrolysis temperature is between 100 and 200° C.

6. The process as claimed in claim 1, wherein the temperature of the cooled outlet tube is between −20° C. and +40° C.

7. The process as claimed in claim 1, wherein the process pressure is in the vacuum range.

8. A process as claimed in claim 1, wherein the resulting formaldehyde vapor is passed through the condensed liquid component collected in the bottom of the evaporator at a temperature of from 100° C. to 200° C.

9. A process as claimed in claim 2, wherein the resulting formaldehyde vapor is passed through the condensed liquid component collected in the bottom of the evaporator at a temperature of from 100° C. to 200° C.

* * * * *